United States Patent [19]

Zanon et al.

[11] Patent Number: 4,934,087
[45] Date of Patent: Jun. 19, 1990

[54] EARTHWORM HARVESTING METHOD

[76] Inventors: Daniel E. Zanon, 8919 Sarah La., Grosse Ile, Mich. 48138; Jesse R. Birchard, 22740 Fireside Ct. #205, Novi, Mich. 48050

[21] Appl. No.: 447,170

[22] Filed: Dec. 7, 1989

[51] Int. Cl.$^5$ ............................................. A01K 97/00
[52] U.S. Cl. ................................................ 43/1; 43/4
[58] Field of Search ....................... 43/1, 4; 424/195.1

[56] References Cited

U.S. PATENT DOCUMENTS

| | | | |
|---|---|---|---|
| 626,890 | 6/1899 | Eaton | 424/195.1 |
| 1,446,914 | 1/1921 | Lingafelter et al. | 43/1 |
| 3,239,413 | 3/1966 | Chaney | 43/1 |
| 4,178,711 | 12/1979 | Mermal et al. | 43/1 |
| 4,556,679 | 12/1985 | Koehler | 514/764 |
| 4,570,372 | 2/1986 | Lukas | 43/1 |

Primary Examiner—Richard K. Seidel
Assistant Examiner—James Miner

[57] ABSTRACT

A method of harvesting earthworms from the ground soil includes forming a solution containing about 1 tablespoon dry mustard, ½ teaspoon cayenne pepper and ¼ teaspoon popcorn salt in 8 oz. of water, pouring the solution on the ground soil or injecting 2 oz. of the solution into a earthworm burrow causing the worms to emerge from the ground.

3 Claims, No Drawings

EARTHWORM HARVESTING METHOD

BACKGROUND OF THE INVENTION

1. Field of the Invention

This invention relates to a method of harvesting earthworms from a ground soil area and to a composition which is effective to encourage earthworms to surface from their burrows while obviating injury to the worms or damage to plant life.

Earthworms conventionally are harvested at night when they emerge from their burrows to move about on the ground surface. Gardens and grass-covered areas such as lawns and meadows usually contain an abundant supply of earthworms. The earthworms are picked, packed and refrigerated and then distributed to various outlets for sale and use primarily as fish bait.

In that worms are nocturnal creatures, harvesting of worms normally must take place at night. Attempts have been made for the commercial harvesting of earthworms during daylight hours by means of the use of an electrical current established in the ground between two electrodes to create a pulsating charge at a predetermined frequency to cause the earthworms to surface. This technique necessitates a high initial capital cost and access to a power supply. In addition, an inexperienced operator is exposed to the hazards of an electrical shock.

DESCRIPTION OF THE PRIOR ART

2. Prior Art

The use of chemical solutions to impregnate ground soil and force earthworms to the surface is known. U.S. Pat. No. 1,446,914 issued Feb. 27, 1923 discloses the application of a lime-sulphur solution containing calcium polysulfide diluted by water to the soil to force earthworms to the surface. U.S. Pat. No. 3,239,413 issued Mar. 8, 1966 discloses a worm lure composition consisting essentially of potassium dichloro-isocyanurate as a chlorine-producing compound preferably together with alkyl aryl sulfonate as a wetting agent and anhydrous sodium tripolyphosphate as a filler. The rate of dissolution of potassium dischloro-isocyanurate in water is difficult to control and can vary ±200%, necessitating the washing of harvested worms and often resulting in the death of the worms within a few days if the dichloro-isocyanurate content in the water is excessive. U.S. Pat. No. 4,178,711 issued Dec. 18, 1979 discloses an aqueous worm harvesting composition containing husks of walnuts mixed with water which is applied to a ground surface area. U.S. Pat. No. 4,556,679 issued Dec. 3, 1985 discloses the application of 1,2,4-trimethylbenzene, which is the irritating agent, and a nonionic surfactant which enables the 1,2,4-trimethylbenzene to mix thoroughly with the water that is added. U.S. Pat. No. 4,570,372 issued Feb. 18, 1986 discloses the application of forming a solution containing about 12 to 30 ppm chlorine in water by dissolving a solid tablet containing by weight about 1 to 10% sodium sulfate and the balance a metal oxychloride in water, pouring the solution on the soil containing worms causing the worms to emerge from the ground.

SUMMARY OF THE INVENTION

The present invention includes a method for causing earthworms to surface from ground soil so they can be harvested. The method includes preparing a composition of dry mustard, cayenne pepper, and popcorn salt mixed with water. This produces a *non-toxic* composition. In testing we observed no injury to the earthworms although we immersed in water all harvested earthworms because of the irritant of the composition.

DESCRIPTION OF THE PREFERRED EMBODIMENTS

The present invention includes a method for causing earthworms to surface from ground soil so that they can be harvested. The method including forming a liquid mixture of 1 tablespoon dry mustard, ½ teaspoon cayenne pepper, ¼ teaspoon popcorn salt and 8 oz. of water and introducing the liquid into a volume of soil. Such introduction of the liquid into the soil will cause earthworms in the soil to come to the surface facilitating convenient harvesting of the earthworms.

In one preferred method, the mixture can be introduced into an earthworm borrow using a 2 teaspoon dropper.

Alternatively, the mixture can be introduced by distributing the mixture over an area of soil using a garden water can.

We claim:

1. A method for causing earthworms to surface from ground soil so they can be conveniently harvested, said method comprising forming a liquid mixture of 1 tablespoon dry mustard, ½ teaspoon cayenne pepper and ¼ teaspoon popcorn salt and 8 oz. of water, and introducing said liquid mixture into earthworm inhabited soil.

2. The method of claim 1 wherein said liquid mixture is introduced into an earthworm borrow in said earthworm inhabited soil using a dropper.

3. The method of claim 1 wherein said liquid mixture is introduced by distributing the same over said earthworm inhabited soil using a garden watering can.

* * * * *